(12) United States Patent
DeLuca et al.

(10) Patent No.: US 6,238,338 B1
(45) Date of Patent: May 29, 2001

(54) BIOSIGNAL MONITORING SYSTEM AND METHOD

(75) Inventors: Carlo J. DeLuca, Wellesley; Per Bergman; Gianluca DeLuca, both of Brookline; L. Donald Gilmore, Wellesley, all of MA (US)

(73) Assignee: Altec, Inc., Boston, MA (US)

( * ) Notice: Subject to any disclaimer, the term of this patent is extended or adjusted under 35 U.S.C. 154(b) by 0 days.

(21) Appl. No.: 09/356,856

(22) Filed: Jul. 19, 1999

(51) Int. Cl.$^7$ .................................................. A61B 5/00
(52) U.S. Cl. ............................................. 600/300; 128/903
(58) Field of Search ........................... 600/300–301, 600/481–486, 544–545; 128/900, 903–904, 920–925

(56) References Cited

U.S. PATENT DOCUMENTS

| | | |
|---|---|---|
| 5,168,871 * | 12/1992 | Grevious ............................. 128/903 |
| 5,464,021 | 11/1995 | Birnbaum . |
| 5,483,967 | 1/1996 | Ohtake . |
| 5,564,429 * | 10/1996 | Bornn et al. ........................ 600/301 |
| 5,634,468 * | 6/1997 | Platt et al. ........................... 128/903 |
| 5,678,545 | 10/1997 | Stratbucker . |
| 5,791,342 | 8/1998 | Woodard . |
| 5,862,803 * | 1/1999 | Besson et al. ....................... 128/903 |
| 5,879,292 | 3/1999 | Sternberg et al. . |

\* cited by examiner

*Primary Examiner*—Eric F. Winakur
*Assistant Examiner*—Michael Astorino
(74) *Attorney, Agent, or Firm*—John E. Toupal; Harold G. Jarcho

(57) ABSTRACT

A biosignal monitoring system including a plurality of sensors for disposition in predetermined positions on the body of a test subject; each sensor having contact surfaces shaped and arranged to detect a particular biosignal generated in the body, a sensor transceiver, a sensor antenna, a voltage supply, and a microprocessor programmed for processing the particular biosignal to provide given data; and a control station providing a wireless, bi-directional data communications link with the sensors; the control station having a station transceiver, a station antenna, and a computer for further processing the given data received from the sensors.

17 Claims, 6 Drawing Sheets

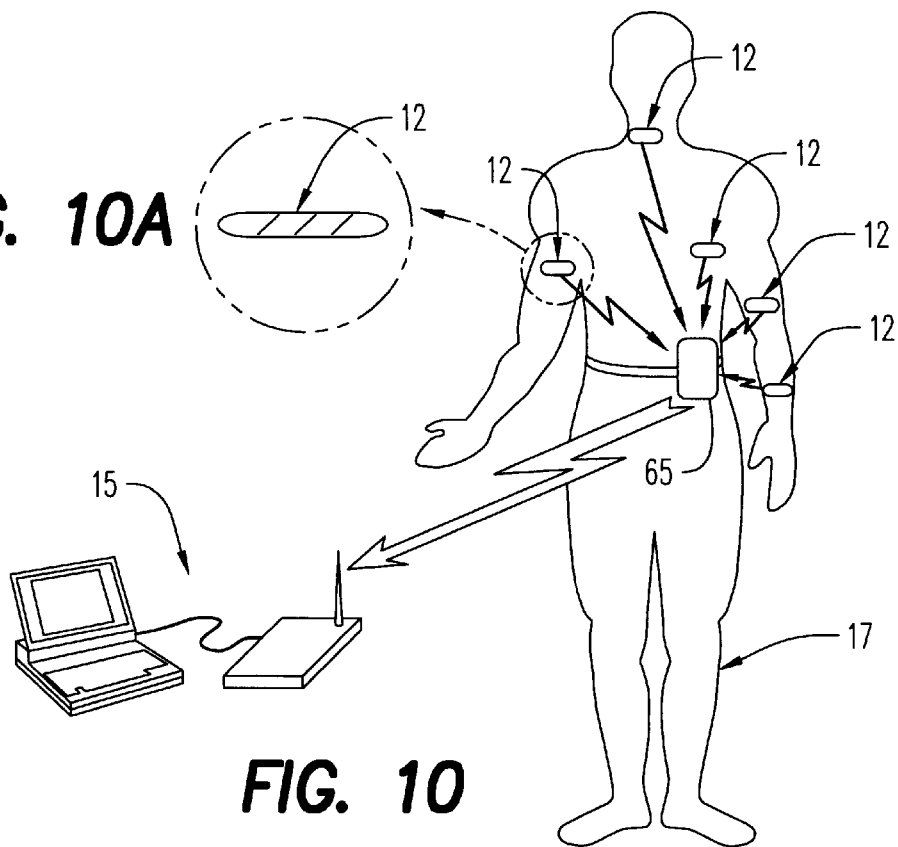
FIG. 10A
FIG. 10
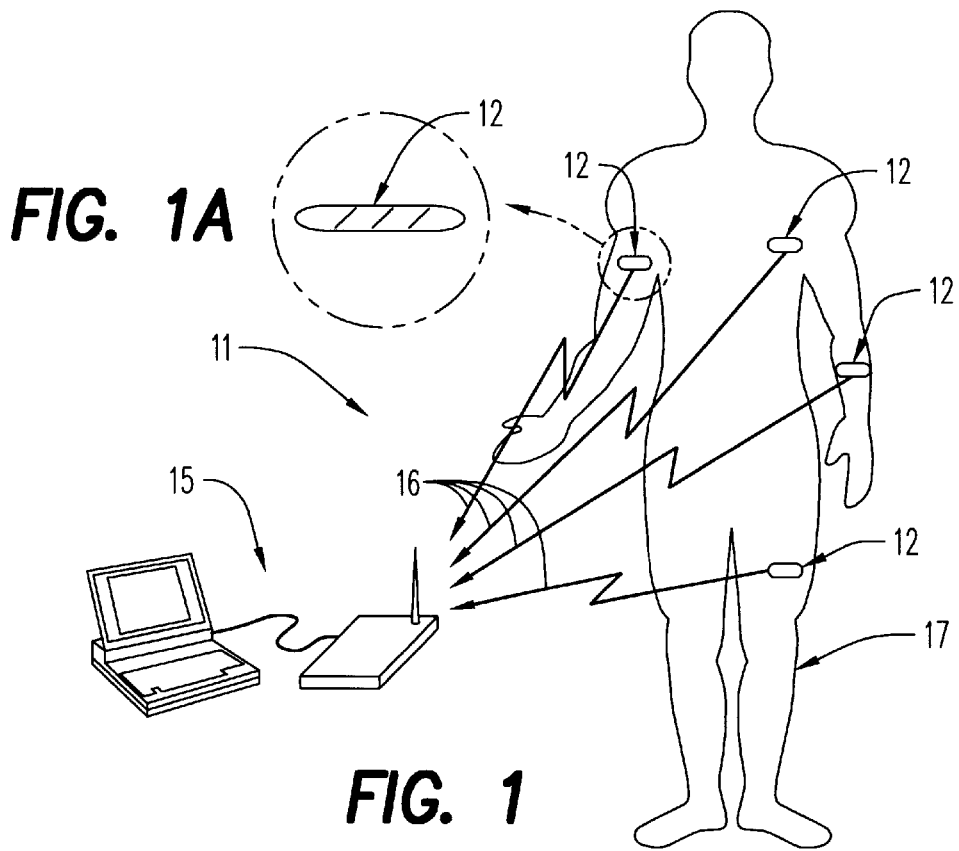
FIG. 1A
FIG. 1

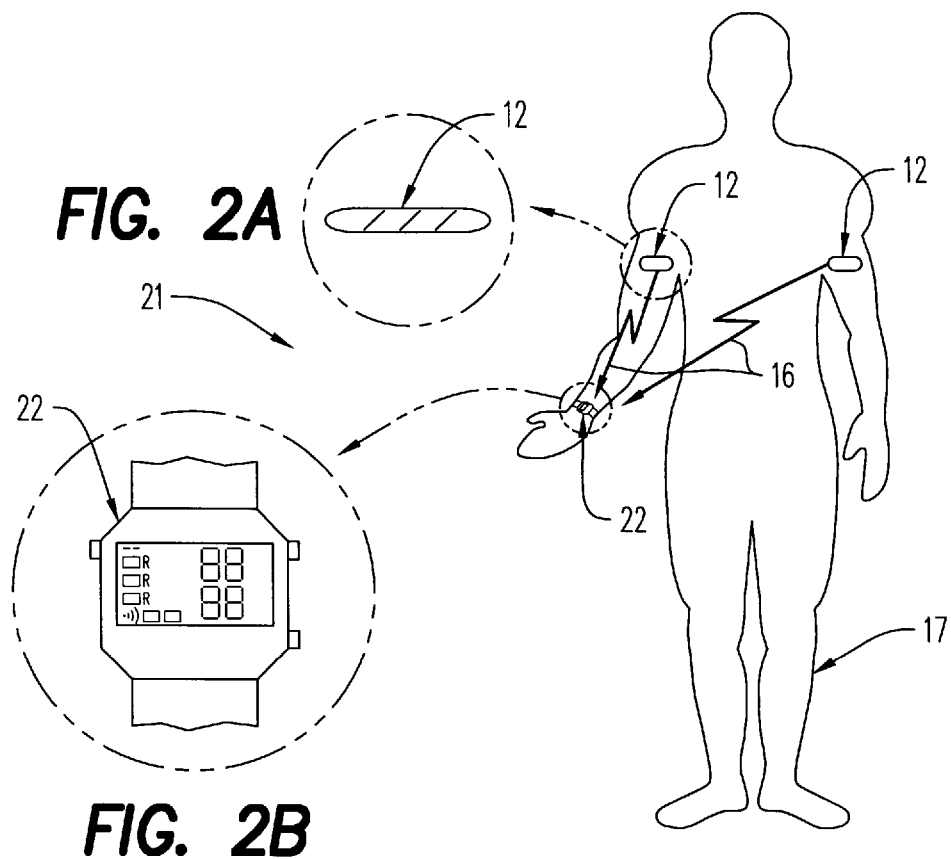
FIG. 2A
FIG. 2B
FIG. 2
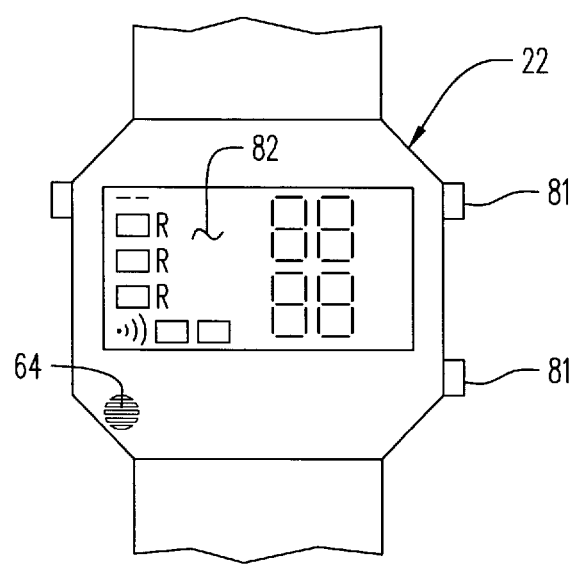
FIG. 9

BIOSIGNAL MONITORING SYSTEM AND METHOD

BACKGROUND OF THE INVENTION

The invention relates generally to a system for monitoring biosignals and, more particularly, to an untethered system for monitoring biosignals of a test subject engaged in a physical activity.

Different biosignals are monitored to detect a variety of physical conditions. Biosignals useful in this regard include, among others, the Electromyographic (EMG) from the muscle, the Electrocardiagraphic (EKG) from the heart, the electroencephalographic (EEG) from the brain, and the Electrooculographic (EOG) from the eyes. Examples of applications entailing biosignal monitoring during physical activity are physical therapies and rehabilitation regimes in the clinical/medical area, strength and fatigue endurance testing in the exercise/fitness area, work related fatigue in the field of ergonomics, muscle performance in research environments, and detection of organophosphates in troops exposed to chemically contaminated battlefields or workers exposed to pesticides and other chemicals commonly used in farm environments. However, biosignal monitoring of subjects engaged in such physical activities has been restricted by the electrical cable tethers utilized between sensors and processing equipment of prior systems.

The object of this invention, therefore, is to provide an improved system for monitoring biosignals from test subjects engaged in various types of physical activity.

SUMMARY OF THE INVENTION

The invention is a biosignal monitoring system including a plurality of sensors for disposition in predetermined positions on the body of a test subject; each sensor having contact surfaces shaped and arranged to detect a particular biosignal generated in the body, a sensor transceiver, a sensor antenna, a voltage supply, and a microprocessor programmed for processing the particular biosignal to provide given data; and a control station providing a wireless, bi-directional data communications link with the sensors; the control station having a station transceiver, a station antenna, and a computer for further processing the given data received from the sensors. The system simplifies monitoring of desired biosignals generated in the body of a test subject engaged in some form of physical activity.

According to other features of the system, the indicator includes a data display and an audible signal generator. The data display and generator provide the subject with data necessary to evaluate certain performance tasks.

According to yet other features of the system, the sensor includes a substrate portion defining the contact surfaces and an adhesive surface for contacting the skin of the test subject; and a circuit board portion mounted on the substrate and including the sensor transceiver, the sensor antenna, and the microprocessor. This sensor is easily applied to a predetermined position on the body of the test subject.

According to still another feature of the invention, the system includes multiple substrates each defining contact surfaces shaped and arranged to detect a different biosignal, the circuit board is adapted for selective interchangeable mounting on each of the multiple substrates, and the microprocessor is selectively programmed to process the particular different biosignal detected by the substrate supporting the circuit board. These features permit a generic circuit board to efficiently monitor various biosignals.

According to a preferred feature of the invention, the different biosignals include EMG, EKG, EEG and EOG signals. These signals provide a variety of data important in the evaluation of a test subject's activities.

According to other features of the invention, the contact surfaces include signal contact surfaces and a reference contact surface and the microprocessor provides the reference contact surface with a driven signal reference; and the microprocessor includes input stages protected from electrostatic discharge. These features enhance operational performance of the system.

According to another feature of the system, the voltage supply comprises a battery and the control station controls charging of the battery via the communication link and the contact surfaces.

The invention also encompasses a method for detecting and processing biosignals including the steps of providing a plurality of substrates, each defining contact surfaces shaped and arranged to detect a different particular biosignal; providing a circuit board including a transceiver, an antenna, a microprocessor, and a voltage supply; selecting one of the substrates; mounting the circuit board on the one substrate to provide a portable unit; selectively programming the microprocessor to process the particular biosignal associated with the selected substrate; and securing the portable unit on a test subject in a manner to facilitate detection of the particular biosignal by the contact surfaces and processing of the detected biosignal by the microprocessor. The method facilitates use of a generic circuit board to effectively monitor various types of biosignals.

BRIEF DESCRIPTION OF THE DRAWINGS

These and other objects and features of the invention will become more apparent upon a perusal of the following description taken in conjunction with the accompanying drawings wherein:

FIG. 1 is a schematic diagram of a biosignal monitoring system according to one embodiment of the invention;

FIG. 1A is a detailed enlarged view of a sensor shown in FIG. 1;

FIG. 2 is a schematic diagram of a biosignal monitoring system according to another embodiment of the invention;

FIG. 2A is a detailed enlarged view of a sensor shown in FIG. 2;

FIG. 9 is a diagrammatic view of a body-worn control station of the biosignal monitoring system shown in FIG. 2;

FIG. 10 is a diagrammatic perspective view of another biosignal monitoring system embodiment of the invention; and FIG. 10A is a detailed enlarged view of a sensor shown in FIG. 10.

DESCRIPTION OF THE PREFERRED EMBODIMENTS

Figure 3:
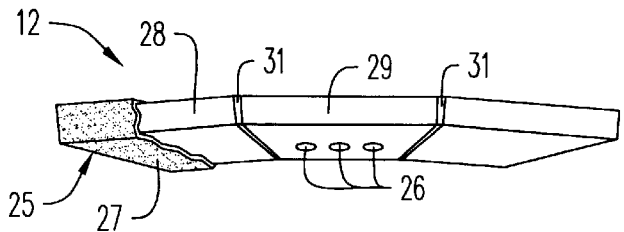
FIG. 3 is a diagrammatic perspective view of a sensor used in the embodiments of FIGS. 1 and 2.

A biosignal monitoring system 11 (FIG. 1) includes a plurality of sensors 12 which communicate with a remote control station 15 via a wireless communication links 16. The sensors 12 in the form of adhesive bandages are secured at predetermined positions on a test subject 17 so as to detect particular desired biosignals generated in the subject's body. Transmissions from the sensors 12 are received and processed as described below by the control station 15.

Illustrated in FIG. 2 is another biosignal monitoring system embodiment 21 in which components common to embodiment 11 (FIG. 1) are identified by the same reference numerals. Again, a plurality of sensors 12 are secured at predetermined positions on a test subject 17 so as to detect particular desired biosignals generated in the subject's body. Those signals are transmitted via wireless communication links 16 to a control station 22. However, in embodiment 21, the control station 22 is in the form of a watch worn on the wrist of the test subject 17.

Figure 3A:
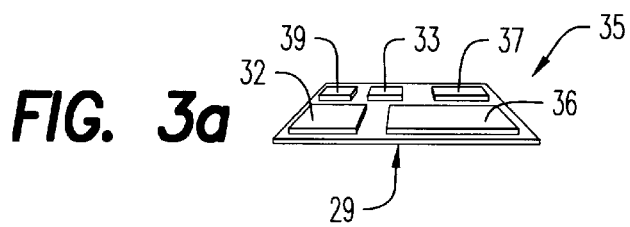
FIG. 3a is a diagrammatic perspective view of a circuit board present in the sensor of FIG. 3.

The sensor 12 (FIG. 3) includes a substrate 25 having exposed, downwardly facing contact surfaces 26 encompassed by an adhesive bottom surface 27. Mounted on the substrate 25 are a battery 28 and circuit board 29 transversely separated by a flexible joint 31. The circuit board 29 (FIG. 3a) includes an RF sensor transceiver chip 32, a sensor antenna chip 33, and a microprocessor chip 35 having an Application Specific Integrated Circuit (ASIC) portion 36 and a System Management portion 37. Also included on the circuit board 29 is an audible alarm 39.

Figure 3B:
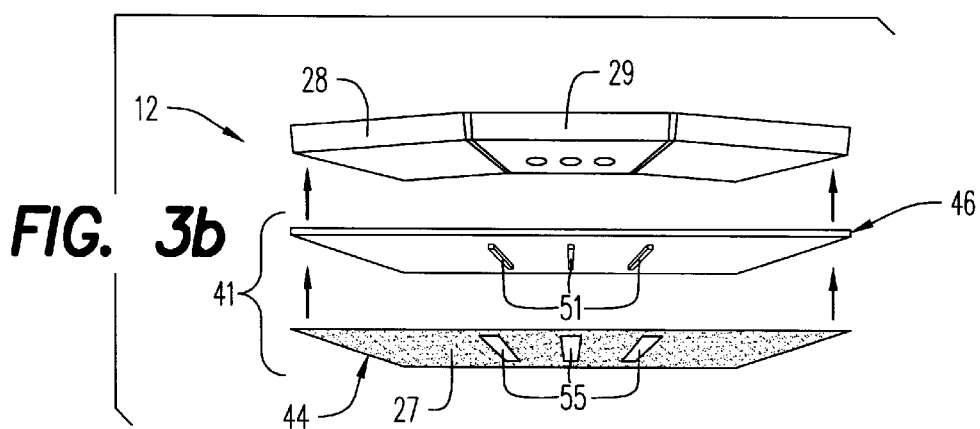
FIGS. 3b and 3c are exploded perspective views illustrating exchangeable contact surface substrates for the sensor shown in FIG. 3.
Figure 3C:
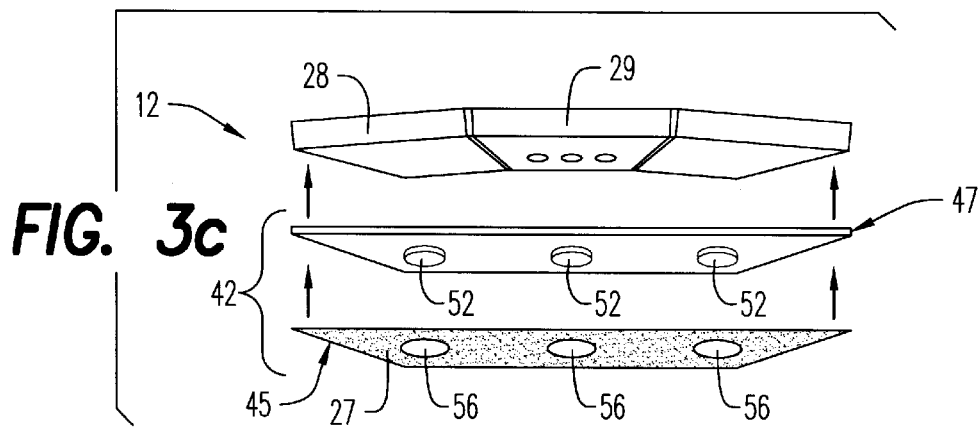

As illustrated in FIGS. 3b and 3c, the sensors 12 preferably include distinct substrate portions 41 and 42 which can be interchangeably combined with the battery 28 and circuit board 29. The substrate portions 41 and 42 consist of, respectively, adhesive interfaces 44 and 45 providing the adhesive surface 27 and sensor substrates 46 and 47. Included in the sensor substrates 46 and 47, respectively, are contacts 51 (FIG. 3b) and 52 (FIG. 3c) for detecting biosignals. The sensor substrates 46 and 47 are straddled by the circuit board 29 and, respectively, the adhesive interfaces 44 and 45. Mated slots 55 and 56 in, respectively, the adhesive interfaces 44 and 45 are aligned with and expose the surfaces of the contacts 51 and 52. The geometrical form of and spacing between the contacts 51 and 52 in, respectively, the sensor interfaces 46 and 47 are distinctly selected to optimally respond to a particular biosignal desired to be detected. Thus, for example, the contacts 51 are elongated and less widely spaced apart than the circular contacts 52 as shown, respectively, in FIGS. 3b and 3c.

The functional elements of the ASIC 36 consist of a memory 54, an input stage 55, signal conditioning stage 56, A/D conversion stage 57, a processing stage 58, and a control stage 59. A power switch 60 connects the battery 28 to the contacts 26 and ASIC 36 and a clock 63 provides timing for the processing stage 58. The overall architecture of the sensor 12 provides a means to individually configure the operating parameters of each stage, and output a resultant processed signal via the bi-directional digital communications links 16 to other devices. As shown, the links are provided by an RF transceiver chip 32. However, other embodiments such as coupling a chip to an additional memory device, or imbedding a chip as a functional component of other sensor systems could be implemented.

By providing a means to remotely configure each stage of the ASIC 36, the performance of the circuitry can be optimized for applications requiring the acquisition of EMG, EKG, or EEG biosignals, or any number of generic applications requiring the acquisition, processing, and alarm limit functions of other low level electrical signal inputs. Within a given application, specific parameters of the output signal (such as raw data, RMS, Mean Absolute Value, Mean and Median frequency, Threshold Value, Beat count, Inter-beat interval, and other parameters which measure the amplitude and frequency characteristics of the detected signals) can be configured and modified during use to optimize data bandwidth, or provide independent stand-alone operation of the sensor 12 with the audio alarm 39 activated when preset signal conditions are exceeded. The low-voltage, low-power design and power management of the ASIC 36 facilitates its use as a component in portable systems using a small single cell battery 28.

Figure 6:
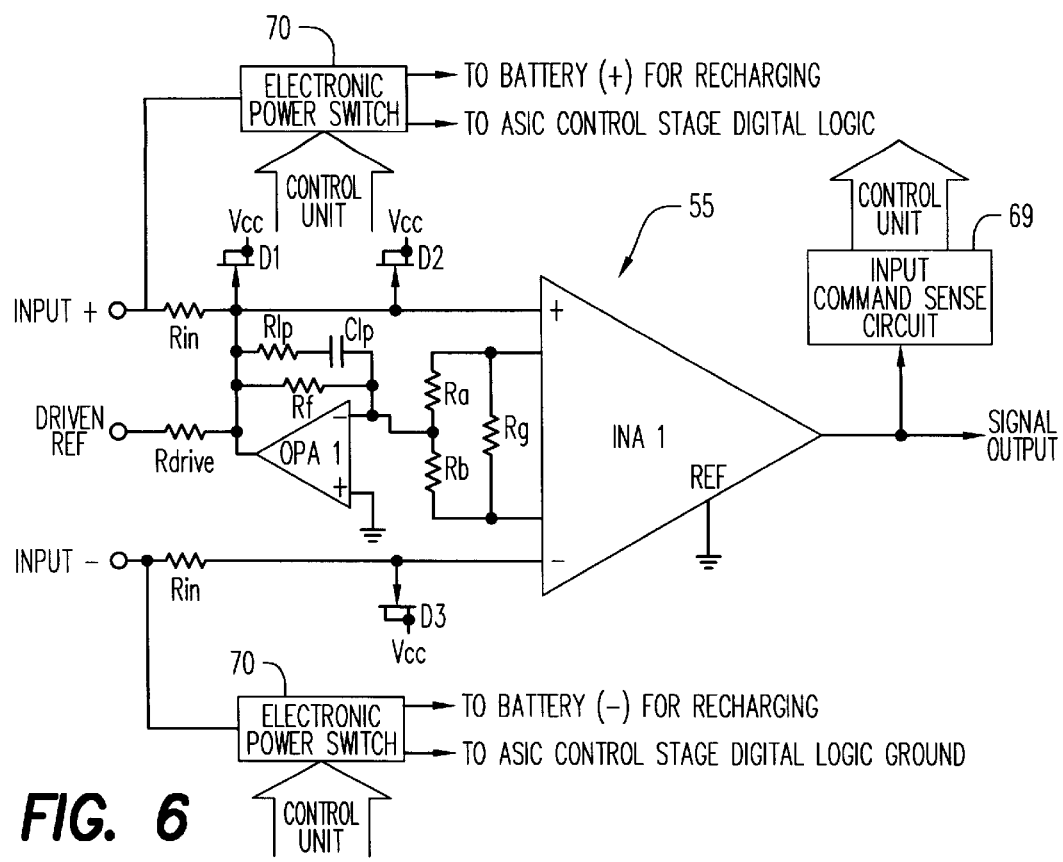
FIG. 6 is a circuit diagram of an input stage of the biosignal sensor depicted in FIG. 5.

The input stage 55 of the ASIC 36 detects low level (microvolts to millivolts), bioelectrical signal voltages from the sensor detection surfaces 26. As shown in FIG. 6, the input stage 55 includes high impedance inputs to minimize the effective loading of the signal source and low input-bias currents to minimize the effects of electrolytic migration resulting from currents flowing through the detection surfaces 26 and body tissue. The circuit 55 has a low noise instrumentation amplifier INA1, with differential inputs INPUT + and INPUT (−), using a driven reference as an input bias current return path. Because of the differential configuration, the effects of any typically encountered common mode signals such as line interference which can be several orders of magnitude greater than the biosignal are reduced. The circuit 55 is provided with a high common mode rejection ratio (CMRR) to maximize the rejection of common mode signal components present within a detected signal.

The driven reference signal DRIVEN REF (FIG. 6) is derived using operational amplifier OPAl, input resistors Ra and Rb, feedback components Rf, Rlp, and Clp, arranged as an inverting amplifier. The common mode voltage sensed by RaandRb is amplified by Rf, filtered by the low-pass filter Rlp and Clp, and coupled to DRIVEN REF through current limiting resistor Rdrive. Because of the driven reference, a voltage is produced at both differential inputs which forces the input common mode voltage to the instrumentation amplifier reference voltage. The driven reference improves the CMMR by reducing the common mode voltage. Because the driven reference produces an equal and opposite voltage in series with the half-cell potentials generated by the components of the skin interface, it reduces the effect of any instability in these potentials due to changing conditions between the detection surfaces and tissue. In addition, all input stage connections to the ASIC 36 are protected against electrostatic discharge by the circuit formed by the current limiting series resistors Rin and Rdrive with their respective diode connected JFETs, D1, D2, D3. This arrangement maintains a low leakage path under normal operating conditions, while providing a current path during overvoltage conditions.

Figure 7:
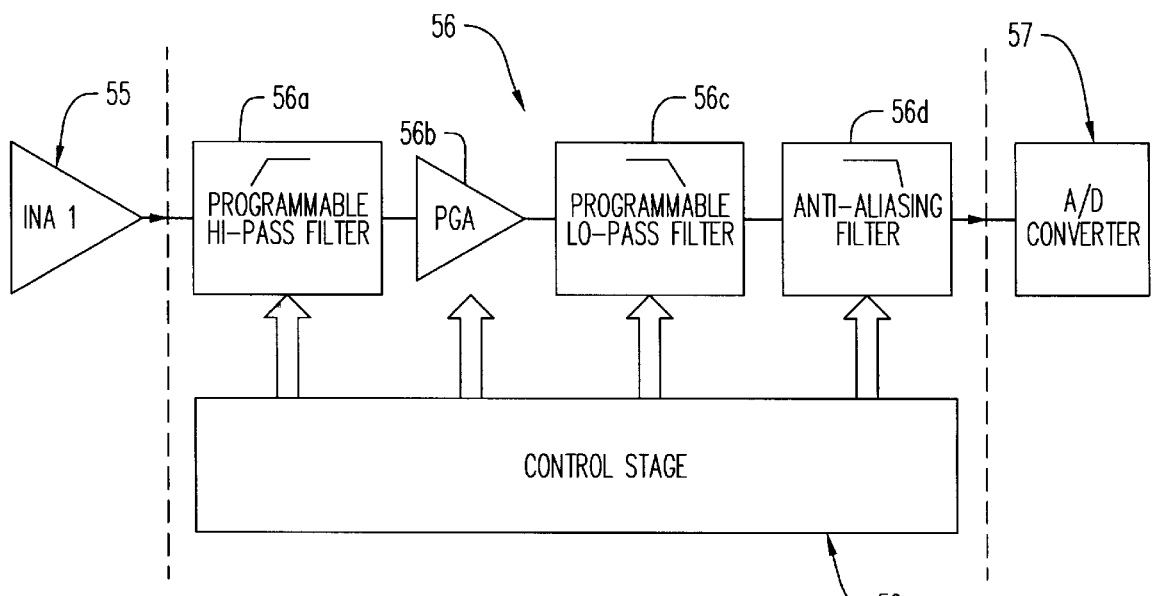
FIG. 7 is a block circuit diagram of a signal conditioner shown in FIG. 5.

The output from the instrumentation amplifier input stage 55 is coupled to the signal conditioning stage 56 which further amplifies and band-pass filters the signal so that it is of suitable voltage range and bandwidth for conversion the A/D converter 57. As shown in FIG. 7 the signal conditioning stage 56 includes a hi-pass filter 56*a*, an amplifier 56*b*, a lo-pass filter 56*c*, and an anti-aliasing filter 56*d*. Each of the filter modules 56*a*, 56*c* and 56*d* is a switched-capacitor filter circuit whose cut-off frequency is determined by the clock frequency at which the filter is switched. The desired clock frequency for each filter module is digitally programmed via the control state 59. The signal output from the input stage 55 is first coupled to the hi-pass filter 56*a* which removes any DC component present in the signal before amplification. Removing the DC component provides a means to amplify low amplitude bio-signals to a level suitable for A/D conversion without exceeding the dynamic range of the A/D converter 57. The hi-pass filter 56*a* can be programmed to provide a DC cutoff frequency for applications requiring DC signal measurement. After hi-pass filtering, the signal is amplified by the programmable gain amplifier (PGA) circuit 56*b*. The gain of the amplifier circuit is determined by the resistance of a resistor network which is digitally programmed via the control stage section 59. Preferably, the gain of the amplifier 56*c* is programmed for a selected application to provide the maximum dynamic range of signal conversion by the A/D converter 57. The output of the amplifier is filtered by the lo-pass filter module 56*c* having a cut-off frequency programmed to provide the optimal signal to noise ratio for a selected application by minimizing the effect of high frequency components outside the range of interest. Before digitization, the signal must be further filtered at a lo-pass cut-off frequency equal to or less than one half the sampling frequency of the A/D converter 57 in order to remove any signal components which would introduce an "alias" in the digitized output. The anti-aliasing filter module 56*d* is programmed to the correct cut-off frequency based on the selected sampling rate. Also, the operating parameters of each module in the signal conditioning stage 56 can be externally programmed via the communications link 16 established with the control stage section 59 of the ASIC 36. The control stage 59 maps the data bits which program the operating parameters to the correct module addresses of the signal conditioning stage 56 where they are stored.

The gain and band-pass filters cut-off frequency parameters can be externally programmed via the communications link 16 established with the Control Stage section 59 of the ASIC 36. Because of the wide selection range of these parameters, the gain and bandwidth of any biosignal can be optimized for a given application. The conditioned signal from conditioner 56 is digitized using the 16 bit A/D converter 57. Resultant 16 bit resolution provides a large dynamic signal range important in sampling low level biosignals contaminated with large artifacts, and minimizes the need to auto-scale gain. The sampling rate can be externally programmed via the communications link 16 established with the Control Stage section 59 of the ASIC 36. In this way the sampling rate can be selected to optimize communications bandwidth and memory storage requirements for a given application The signal processing stage 58 calculates any one of the following parameters; Digitized Raw Signal, RMS, Mean Absolute Value, Mean and Median frequency, Threshold Value, Beat count, Inter-beat interval, and other parameters which measure the amplitude and frequency characteristics of the detected signals. Algorithms for calculating these parameters can be externally programmed via the communications link 16 established with the Control Stage section 59 of the ASIC 36, and the resultant output transferred to the Control Stage section 59 for transmission or for storage in on-board memory. A microcomputer 68 manages all the functions of the control station 15 including selection and modification of applications programs, sensor communications, signal processing, data storage, and activation of audio and visual alarms 64, 65. It provides an interface 76 for user input and display, and an I/O interface 66 for peripheral devices such as a lap top computer 85. These functions may in part, be implemented by one or more embedded processors.

The control stations 15, 22 of, respectively, system embodiments 11, 21 oversee the management of functions relating to the control, data acquisition and signal processing for all the sensors 1–12. As shown in FIGS. 1 and 2, respectively, a control station may be realized as a remote freestanding unit 15 with an integral docking station 71 for storing and charging multiple sensors 12 or can be realized as a "wrist-watch" type device 21 worn by the subject 17. In one configuration, the freestanding station 15 would be part of an autonomous system which would monitor selected biosignals, make intelligent decisions regarding any conditions requiring action, such as triggering a local audio or visual alarm, log all the data, and/or contact a central network where the data could be downloaded for further interpretation. Conversely, when configured as a wrist worn unit 21, the station would be programmed to provide its wearer with real-time audible/visual feedback of selected parameters and task compliance. The display could instruct the test subject 17 through a sequence of tasks, provide feedback during the task, and based on real-time analysis of the acquired data, give audio warnings and visual recommendations for specific actions required.

Figure 4:
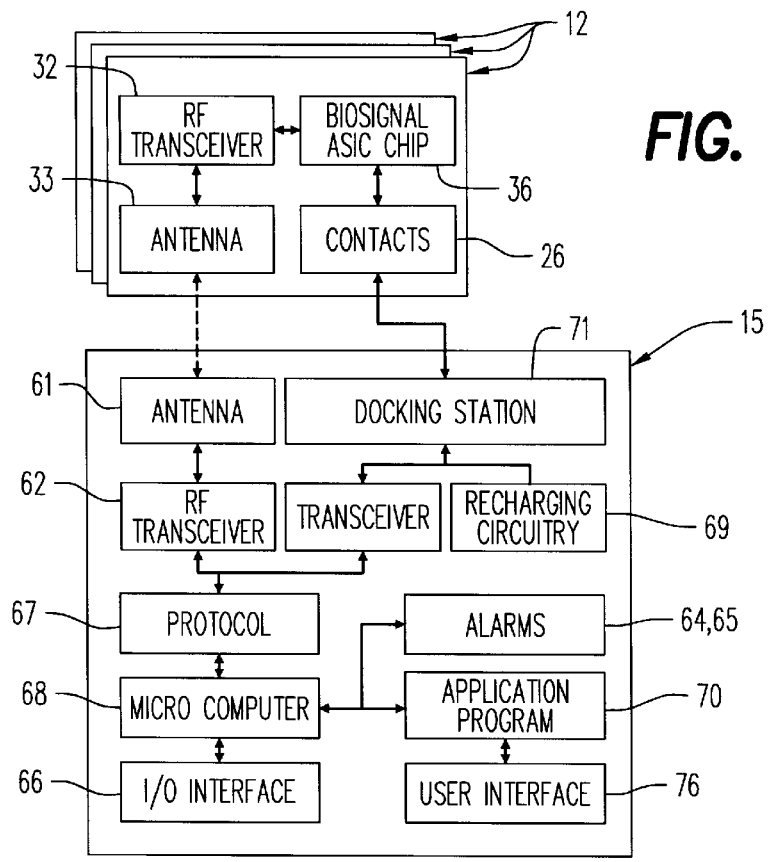
FIG. 4 is a block circuit diagram of the biosignal monitoring system shown in FIGS. 1 and 2.
Figure 5:
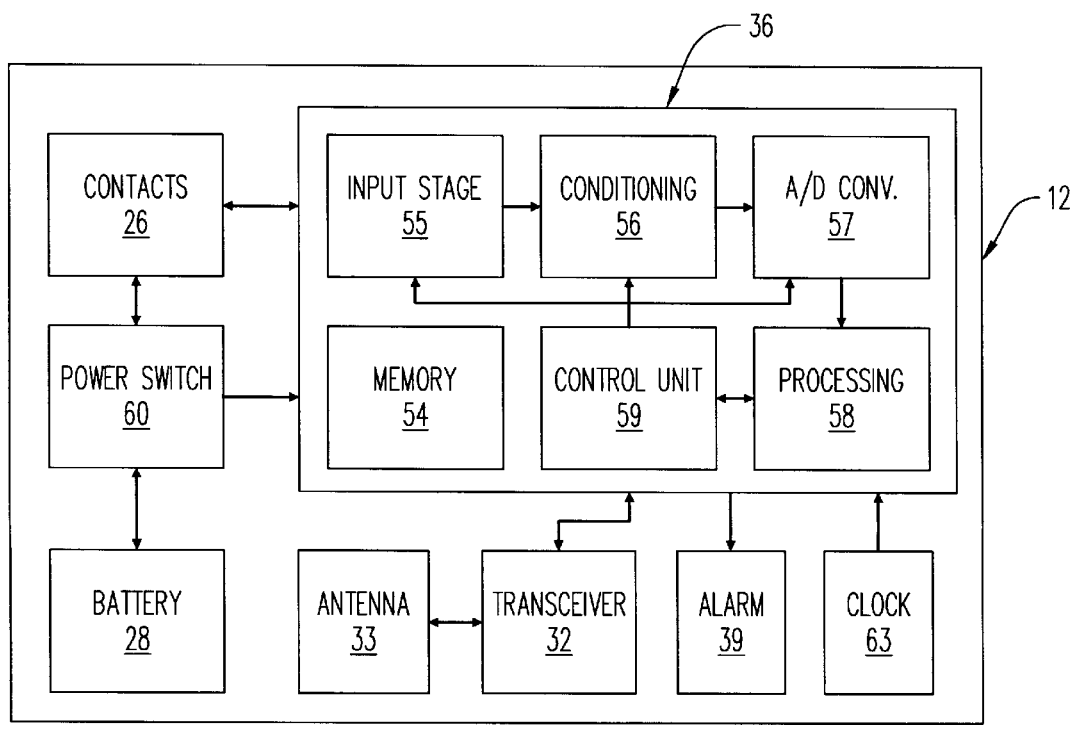
FIG. 5 is a block circuit diagram of a biosignal sensor used in the monitoring system of FIG. 4.

Both the free standing and wrist worn versions of the stations 15, 22 have the same basic architecture shown in FIG. 4. The primary functional differences are that the free standing station 15 has an integrated docking station for recharging, and directly programming the multiple sensors 12, a more comprehensive visual display, and larger memory capacity for logging data. Both of the stations 15 and 22 can communicate with other peripheral devices such as printers or other computers. Typical communication would be established via standard serial, parallel or Infra-Red link (such as in the wrist worn station 22). Applications in which the wrist worn station 22 is used would have a reduced subset of program functions and have a simpler, separate version of a docking station to recharge batteries 28, or could use sensors 12 with disposable batteries.

When the biosignal sensors 12 are attached to the test subject 17 and used with the control station 15 (FIG. 4), a short range (<50 m) bi-directional communications link 16 is established between each sensor 12 via an antenna 61 and RF transceiver 62. For applications where the station 15 is located at a greater distance from the sensors 12, an RF repeater 65 (FIG. 10) can be worn by the subject 17 to increase transmission range. The communications protocol for transfer of information between the control station 15 and each of the sensors 12 or between the control station and the repeater 65, is determined by protocol software programs 67 and an embedded microcomputer 68. This protocol also adjusts the transmitter output power to provide an optimal balance between operating distance, and operating time of the sensor in the presence of RF background interference. A docking station 71 component of the control station 15 establishes direct electrical connections to the sensor 12 input contacts 26. These connections function to: 1) Recharge the sensors batteries 28. 2) Assign a unique ID code. 3) Verify calibration and status of the sensors 12. 4) Download the program for a selected application into the Sensor memory 54.

Figures 8, 8A:
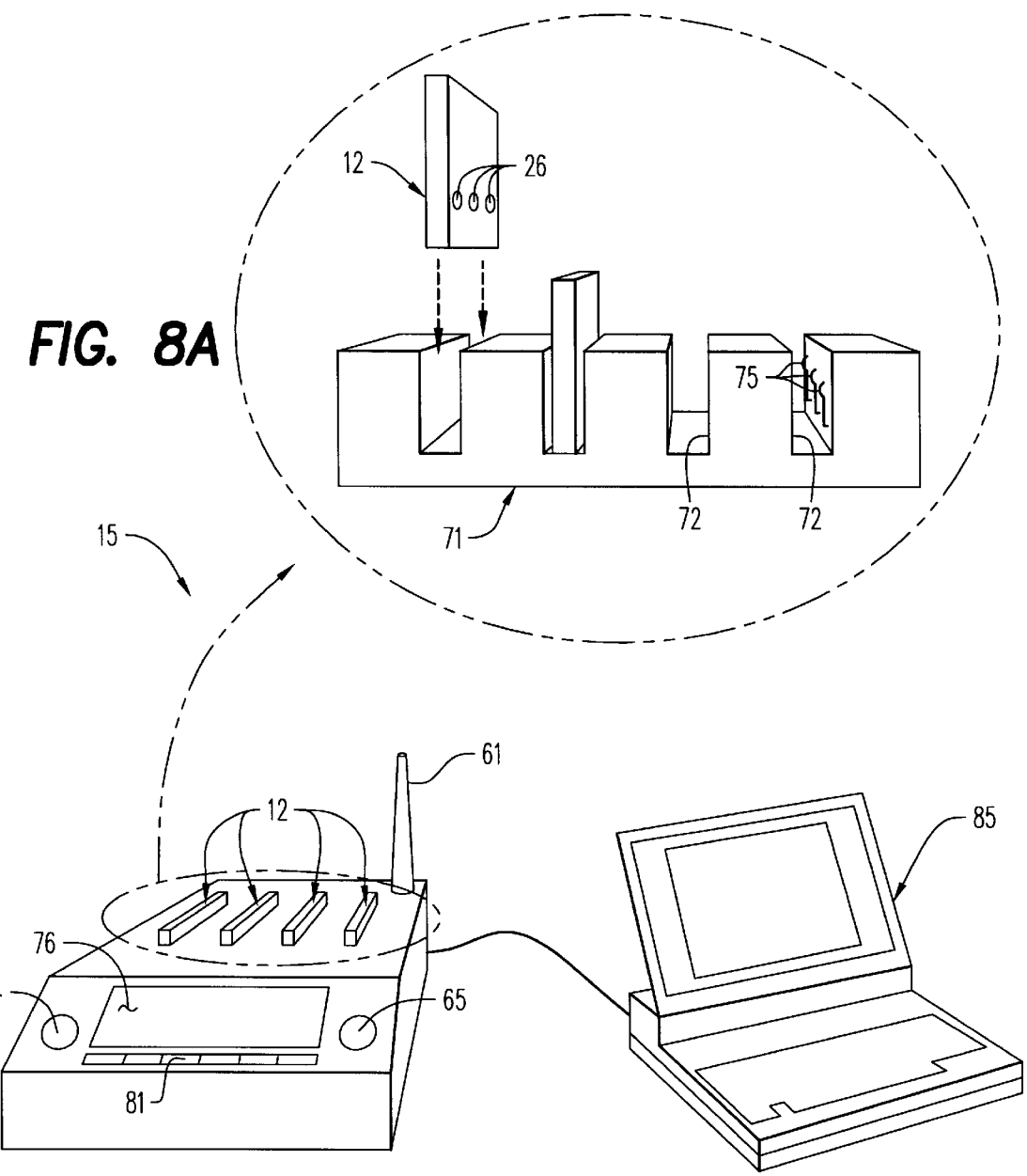
FIG. 8 is a diagrammatic perspective view of a remote control station of the biosignal monitoring system illustrated in FIG. 1.
FIG. 8A is a detailed enlarged view of a docking system shown in FIG. 8.

The circuitry for communicating and recharging the battery 28 through the sensor input contacts 26 is shown in FIG. 6. This circuitry consists of input command sense circuit 69 and an electronic power switch 70 both controlled by the control unit 59 of the ASIC 36. When a sensor insertion is detected by the receptacle 72 of the docking station 71, (FIG. 8) an analog "request for communication" command signal is issued through the mating contacts 75 of the docking station 71. This signal is sensed by the (+) and reference input contacts of the input stage 55 and the resultant output coupled to the input command sense circuit 69 which decodes the analog command signal from the docking station 71 and sends a request for communication to the control unit 59 of the ASIC 36. The control unit 59 then activates bi-directional electronic switches connected to the input contacts 26 to select either a serial digital signal path to the digital logic input/output of the ASIC 36 for transfer of I.D. code, program and setup data, or select a path to the sensors battery 28 for recharging by the recharging circuit residing in the docking station 71. During the recharging phase, the state of charge is monitored by the recharging circuit of the docking station 71 and the status is displayed on the display 76 of the base station 15. If the sensor's battery 28 is completely discharged and communication cannot be established, the recharging circuit in the docking station 71 will automatically place the sensor 12 in recharge mode via steering diodes in the electronic power switches 70 until the sensor 12 is recharged and will then reinitialize the sensor 12.

In one embodiment, the docking station 71 can be a module (FIG. 7) with multiple slots 72 slightly larger than the width of sensor 12. A set of compliant matching contacts 75 on the inner sides of each slot 72 mates with the contacts 26 of a sensor 12 and holds it firmly in place when inserted into the slot 72. The geometry of each slot 72 is configured so as to ensure proper registration of the sensor contacts 26 with respect to the contacts 75 of the slot. Once mechanical insertion has been completed, a user interface display 76 acknowledges if electrical contact has been successful, and determines the charge status of the sensor battery 28. After full charging of the battery, the program performs any other required configuration of the sensor 12 and indicates to the user that the sensor is ready to use. When a sensor 12 is removed from the docking station 71, the RF communications link 16 is re-established with the control station 15 which controls the transfer of data to and from all the individual sensors 12 attached to the subject 17. If the control station is in the form of a wrist worn device 22, the docking station could be a separate unit to recharge sensor batteries. Selecting and re-programming each sensor from a multiple array in this configuration requires a two step procedure: First, the RF transceiver in the wrist worn unit 22 is used to send a command to the docking station requesting it to select an individual sensor docking slot. The docking station would enable the RF transceiver of the selected sensor in that slot using its direct electrical connection with the sensor. Second, the RF transceiver in the wrist worn unit would establish an RF communications link with the enabled sensor to program the ID and other desired functions. This procedure would be repeated until all the sensors are re-programmed.

Operation

The operating functions performed by the sensors 12 are programmed using the bi-directional communications link managed by the control stage 59 of the ASIC 36. A communications link can be established via direct electrical connection used for the sensor input contacts 26 (FIG. 8), or via an RF link 16 established with a remote control station 15 (FIG. 1). The direct electrical connection provides a means for assigning an ID code and verifying calibration of the sensor 12 when docked in its recharging station. During this time the configuration program for a selected application can be automatically downloaded into the sensor memory 54. When the sensor 12 is removed from the docking station 71, the RF communications link 16 is re-established with the control station 15 which controls the transfer of data to and from all the individual sensors 12 attached to the subject 17. Under command of the control station 15, the configuration program of the attached sensor 12 can be modified to select different signal conditioning parameters and sampling rates, and to perform a different set of signal processing functions.

The ability to unobtrusively modify the operating parameters of a sensor 12 while it is still attached to the subject 17, facilitates optimization of sensor performance in terms of transmission range, bandwidth, and operating time, without compromising the ability to examine signal data in detail using full system bandwidth, processing power and the decision making capacity resources of the control station computer 68. Based on that detailed information, the control station 15 can reset limit threshold parameters for the sensor alarm function and re-select appropriate signal processing algorithms for a given application.

An example of an application in which a sequence of different output parameters are selected, would be the use of the sensor 12 to monitor EKG signals. A typical output parameter of interest would be heart rate. Periodically, or based on limit criteria such as a preset heart rate, each sensor 12 would be commanded by the control station 15 to reconfigure its program to transmit several seconds of the entire EKG signal wave form for more detailed analysis. The advantage of this technique is that it provides all the necessary information required for the application while greatly reducing the average data bandwidth and prolonging operating time for the sensor 12.

In addition to selecting the appropriate data acquisition parameters such as gain, bandwidth and sampling rate, the signal processing algorithms with their associated coefficients can be selected via the RF communications links 16 established with the control stage 59 section of the ASIC chip 36. The signal processing stage 58 calculates any one of the following output parameters: Digitized Raw Signal, RMS, Mean Absolute Value, Mean and Median frequency, Threshold Value, Beat count, Inter-beat interval, and other parameters which measure the amplitude and frequency characteristics of the detected signals. Resultant processed signal output can be selected for transmission to the control station 15 or stored in on-board memory 54.

The communications links 16 also control power management functions for the battery 28 and transceiver 32 of each sensor 12. When a sensor 12 is in the docking station 71 of the control station 15 (FIG. 7) a direct link established with the sensor contacts 26 controls the power switching of the battery 28, so that the sensor 12 can be recharged by the charger 69 in the control station. The sensor transceiver section 32 is powered down to a "sleep mode" during charging. When the sensor 12 is fully charged and removed from the docking station 71, it is in "watch dog" mode waiting to be activated for use by a command from the control station RF transceiver 62. Subsequently, the sensor 12 can be activated for use and the control station 15 can select the output level for the sensor transmitter 32 based on the desired transmission distance and level of RF background interference. Varying the output power level of the sensors transmitter 32 greatly effects sensor operating time, the incidence of data transmission errors, and conflicts with nearby systems. Real-time control of transmitter output level facilitates a balance of data integrity and operating time as operating conditions change.

A user interacts with the control station 15 via the dot matrix display 76 with "soft" keys 81. Each key 81 is mapped to an area of the display which defines its current action. In this way, only a few separate keys are required to access all the display functions used to select and control the program. In addition to accessing the program, the display provides other types of information to the user in alphanumeric test and graphics formats. When using the wrist worn control station 22 (FIG. 9) a display 82 would present processed parameters as real-time feedback to the test subject 17 as a bar graph or number which is representative of his performance level. When configured as a free standing control station 15 with docking station 71, the display 76 could provide more comprehensive interaction and control of functions such as battery recharge status, ID assignment, and data logging. In addition, a peripheral device such as a lap top computer 85 could assume display and keyboard functions of the control station.

Applications

A selection of general applications for the system 11 is stored in the program memory 70 of the control station 15. These programs optimally configure and modify all the operating parameters for the sensor 12 and signal processing algorithms required for the designated application. Depending on the application, the resultant data output to the user could be in the form of a visual display, audio alarm, or file stored locally or transferred to other peripheral devices in the system. The classes of typical applications include programs for basic research, clinical/medical use (such as diagnosis and treatment outcome), consumer sports and fitness, commercial job task evaluation and ergonomics, and military applications monitoring task performance and tele-operator control. The control station 15 can be initially programmed with a subset of programs selected from a larger computer library of applications from a given class.

Use examples for the subject worn control station 22 are clinical applications in which the sensors 12 are positioned to detect EMG signals and: 1) Provide feedback to the subject 17 proportional to the level of muscle activity for purposes of training muscles to properly contract or relax, 2) Set alarm limit conditions to ensure a safe level of muscle activity when exercising with injury, and 3) Integrate and display the information from multiple muscle sites such as agonist/antagonist pairs as an aid in improving muscular coordination. Using real-time feedback information provided by the system 21, the subject 17 can take a more active role in his rehabilitation process, and a clinician can verify compliance.

In another application example, the wrist worn control station 21 would be used with an EKG programmed signal sensor 12 to display heart rate parameters and set maximum heart rate alarm limits during exercise. In addition to these simple heart rate displays, the station 21 could be programmed to analyze more complex heart performance parameters based on interpretation of signal wave forms, and set a desired alarm function and log data for later diagnosis by a physician. Still other applications for the systems 11 and 21 include determinations using EMG signals of: 1) when a specific muscle is activated to the programmed level; 2) when a multiple of muscles are each activated to a programmed level; 3) when the time sequence of a multiple of muscles is activated according to a programmed time sequence; 4) when both the amplitude and time sequence of a multitude of muscles is activated according to a programmed time sequence; determinations using EKG signals of: 1) when the heart beats continuously; 2) when the heart rate surpasses a programmed level; 3) display the EKG action potential; 4) when the heart beat becomes irregular or too regular according to normative setting or according to a programmed level; and use of EEG signals to determine: 1) when the alpha, beta, theta waves (and other components) of the EEG signal have excursions outside preset thresholds and display the frequency of these waves; and 2) when parameters, such as the RMS, Mean Rectified Value, have excursions outside preset thresholds, and display other relevant measurements which are commonly related to the EEG signals.

Obviously, many modifications and variations of the present invention are possible in light of the above teachings. It is to be understood, therefore, that the invention can be practiced otherwise than as specifically described.

What is claimed is:

1. A biosignal monitoring system comprising:
   a plurality of sensors for independent disposition in predetermined positions on different muscles in the body of a test subject; each said sensor comprising contact surfaces shaped and arranged to detect a particular EMG biosignal generated in the different muscle on which it is disposed, a sensor transceiver, a sensor antenna, a voltage supply, and a microprocessor programmed for processing said particular EMG biosignal to provide given data for identifying given movements of the test subject; and
   control station means providing a wireless, bi-directional data communications link with each of said sensors; said control station means comprising a base station including a station transceiver, a station antenna, and computer means for further processing said given data received from said sensors and a portable repeater adapted to be worn by the test subject and to provide wireless bi-directional communication between said sensors and said base station.

2. A system according to claim 1 wherein each said sensor comprises a substrate portion defining said contact surfaces and an adhesive surface for contacting the skin of the test subject; and an associated circuit board portion mounted on said substrate and including said sensor transceiver, said sensor antenna, and said microprocessor.

3. A system according to claim 2 wherein said substrate portions each define contact surfaces shaped and arranged to detect a different said biosignal, and each said circuit board portion is adapted for selective interchangeable mounting on any of said multiple substrates.

4. A system according to claim 3 wherein each said microprocessor is selectively programmed to process the particular said different biosignal detected by said associated substrate portion.

5. A system according to claim 1 wherein said contact surfaces comprise signal contact surfaces and a reference contact surface; and said microprocessor is adapted to provide said reference contact surface with a driven signal reference.

6. A system according to claim 1 wherein each said microprocessor comprises input stages, and protection circuit means for protecting said input stages from electrostatic discharge.

7. A system according to claim 1 wherein each said microprocessor provides an overall gain controlled by said control station means via said communications link.

8. A system according to claim 1 wherein each said microprocessor comprises filter network means having a bandwidth controlled by said control station means via said communications link.

9. A system according to claim 1 wherein each said microprocessor comprises an A/D converter with a sampling rate controlled by said control station means via said communications link.

10. A system according to claim 1 wherein said communication link includes said contact surfaces.

11. A method for detecting and processing biosignals comprising the steps of:

providing a plurality of substrates, each defining contact surfaces differently shaped and arranged to detect a different particular biosignal;

providing a particular circuit board comprising a transceiver, an antenna, a microprocessor, and a voltage supply; and shaped and arranged for mounting on any of said substrates to provide interconnection with said contact surfaces thereon;

selecting one of said substrates;

mounting said particular circuit board on said one substrate to provide a portable unit;

selectively programming said microprocessor on said one circuit board to process the particular biosignal associated with said selected substrate; and securing said portable unit on a test subject in a manner to facilitate detection of said particular biosignal by said contact surfaces and processing of said detected biosignal by said microprocessor.

12. A method according to claim 11 including the step of selecting one or more additional said substrates; mounting one of said particular circuit boards on each of said additional substrates to provide one or more additional portable units; selectively programming the microprocessor on each of said additional circuit boards to process the particular biosignal associated therewith; and securing each said additional unit on a test subject.

13. A biosignal monitoring system comprising:

a plurality of sensor substrates for disposition in predetermined positions on the body of a test subject; each said sensor substrate defining contact surfaces shaped and arranged to detect a different biosignal generated in the body; and a plurality of circuit boards each retaining a transceiver, an antenna, a voltage supply, and a microprocessor programmable for processing any of said different biosignals to provide given data; and each said circuit board being adapted for selective interchangeable mounting on any of said substrate portions so as to establish electrical connection with said contact surfaces.

14. A biosignal monitoring system comprising:

a plurality of sensors for disposition in predetermined positions on the body of a test subject; each said sensor comprising contact surfaces shaped and arranged to detect a particular biosignal generated in the body, a sensor transceiver, a sensor antenna, a voltage supply, and a microprocessor programmed for processing said particular biosignal to provide given data; and wherein said contact surfaces comprise signal contact surfaces and a reference contact surface; and said microprocessor is adapted to provide said reference contact surface with a driven signal reference; and control station means providing a wireless, bi-directional data communications link with said sensors; said control station means comprising a station transceiver, a station antenna, and computer means for further processing said given data received from said sensors.

15. A biosignal monitoring system comprising:

a plurality of sensors for disposition in predetermined positions on the body of a test subject; each said sensor comprising contact surfaces shaped and arranged to detect a particular biosignal generated in the body, a sensor transceiver, a sensor antenna, a voltage supply, and a microprocessor programmed for processing said particular biosignal to provide given data; and control station means providing a wireless, bi-directional data communications link with said sensors; said control station means comprising a station transceiver, a station antenna, and computer means for further processing said given data received from said sensors; and wherein said microprocessor comprises filter network means having a bandwidth controlled by said control station means via said communications link.

16. A biosignal monitoring system comprising:

a plurality of sensors for disposition in predetermined positions on the body of a test subject; each said sensor comprising contact surfaces shaped and arranged to detect a particular biosignal generated in the body, a sensor transceiver, a sensor antenna, a voltage supply, and a microprocessor programmed for processing said particular biosignal to provide given data; and control station means providing a wireless, bi-directional data communications link with said sensors; said control station means comprising a station transceiver, a station antenna, and computer means for further processing said given data received from said sensors; and wherein said microprocessor comprises an A/D converter with a sampling rate controlled by said control station means via said communications link.

17. A biosignal monitoring system comprising:

a plurality of sensors for disposition in predetermined positions on the body of a test subject; each said sensor comprising contact surfaces shaped and arranged to detect a particular biosignal generated in the body, a sensor transceiver, a sensor antenna, a voltage supply, and a microprocessor programmed for processing said particular biosignal to provide given data; and control station means providing a wireless, bi-directional data communications link with said sensors; said control station means comprising a station transceiver, a station antenna, and computer means for further processing said given data received from said sensors; and wherein said communications link includes said contact surfaces.

* * * * *